US00PP36061P2

(12) United States Plant Patent
Hansen

(10) Patent No.: US PP36,061 P2
(45) Date of Patent: Aug. 6, 2024

(54) ***ACHILLEA* PLANT NAMED 'Firefly Red Pop'**

(50) Latin Name: ***Achillea* hybrid**
Varietal Denomination: Firefly Red Pop

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,759

(22) Filed: Jan. 22, 2024

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 6/14; A01H 5/02
See application file for complete search history.

*Primary Examiner* — Keith O. Robinson

(57) ABSTRACT

A new and distinct Yarrow, *Achillea* plant named 'Firefly Red Pop', with a billowy habit, silvery-green, moderately-dissected foliage and large, bright cherry-reddish florets on heavily-branched compound corymbs, narrow, dark green, fern-like foliage; tall, stiff, beginning in late June and continuing for about seven weeks and repeating if dead-headed. The new plant is useful for landscaping, as a specimen or en masse, and as a cut flower.

1 Drawing Sheet

Botanical designation: *Achillea* hybrid.
Cultivar denomination: 'Firefly Red Pop'.

STATEMENT REGARDING PRIOR DISCLOSURES UNDER 37 CFR 1.77(b)(6)

The first offer for sale was made by Walters Gardens, Inc. on May 8, 2023. Subsequently, on Dec. 1, 2023, the claimed plant was displayed as a photograph with a brief description on a website operated by Walters Gardens, Inc. Walters Gardens, Inc. obtained the plant and all information relating thereto, from the inventor. No plants of *Achillea* 'Firefly Red Pop' have been sold, in this country or anywhere in the world nor has any disclosure of the new plant been made more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Firefly Red Pop', by the cultivar name, 'Firefly Red Pop', or as the new plant. The new plant was selected by the inventor as a single seedling resulting from a self-pollination of a proprietary, unreleased, unnamed seedling known only by the breeder code 13-5-26 (not patented) in a research facility of a wholesale perennial grower based in Zeeland, MI, USA. The cross was performed in the summer of 2014, and the seeds from this cross were collected on Sep. 23, 2014. The seedlings were then isolated and compared in subsequent years to other Yarrow and subsequently found to be different from all cultivars known to the discoverer and eventually given the breeder code 14-38-x before naming 'Firefly Red Pop'.

Asexual propagation at the same nursery in Zeeland, MI, USA by division since August of 2016 and later by shoot tip cuttings shown 'Firefly Red Pop' to be stable and reproduce true to type in successive generations.

SUMMARY OF THE PLANT

*Achillea* 'Firefly Red Pop' has not been observed in all possible environmental conditions. The phenotype may vary slightly with changes in environments such as light intensity, fertility, water availability, etc. without any variation in genotype.

*Achillea* 'Firefly Red Pop' is distinct from all cultivars known to the inventor in the following traits:

1. Billowy habit about 68 cm tall and 109 cm wide;
2. Silvery-green dissected foliage;
3. Heavily-branched peduncles with broad clusters of inflorescences;
4. Large, bright cherry-red ray florets surround small yellow eyes;
5. Sturdy stems withstand wind and rain;
6. Long flowering period beginning late June and continuing for about seven weeks;
7. Repeat flowering if deadheaded.

Plants of *Achillea* 'Firefly Red Pop' are most similar to 'Balvinred' U.S. Plant Pat. No. 25,618, 'Strawberry Seduction' U.S. Plant Pat. No. 18,401, 'Pomegranate' (not patented) and 'Heartthrob' U.S. Plant Pat. No. 32,089.

'Balvinred' is smaller in habit, both shorter and narrower than the new plant, and the ray florets mature to a darker reddish-purple. 'Strawberry Seduction' has a smaller habit and the ray floret color begins yellowish and changes significantly to mature to a purplish-red. 'Pomegranate' has a slightly smaller habit with dark reddish flowers. 'Heartthrob' has a smaller habit and the floret colors that are more orangish-red. The foliage on all these listed comparison cultivars is more finely dissected and the lobes are narrower.

The parent selection was more open and less upright in habit with ray florets that are more reddish purple.

BRIEF DESCRIPTION OF THE DRAWINGS

The color drawings illustrate the overall characteristics of *Achillea* 'Firefly Red Pop' as a three-year-old plant in a full-sun trial garden in Zeeland, Michigan. The colors are as true as reasonably possible given the technology available. The color values may vary slightly depending on light intensity and quality.

DETAILED BOTANICAL DESCRIPTION

Figure 1:
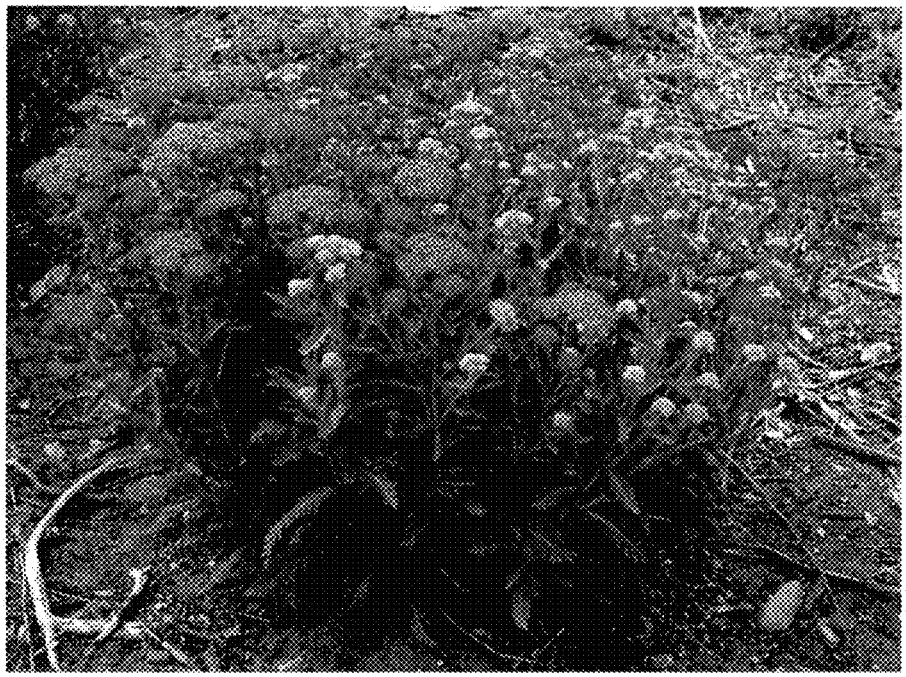
FIG. 1 shows the new plant in a trial facility.
Figure 2:
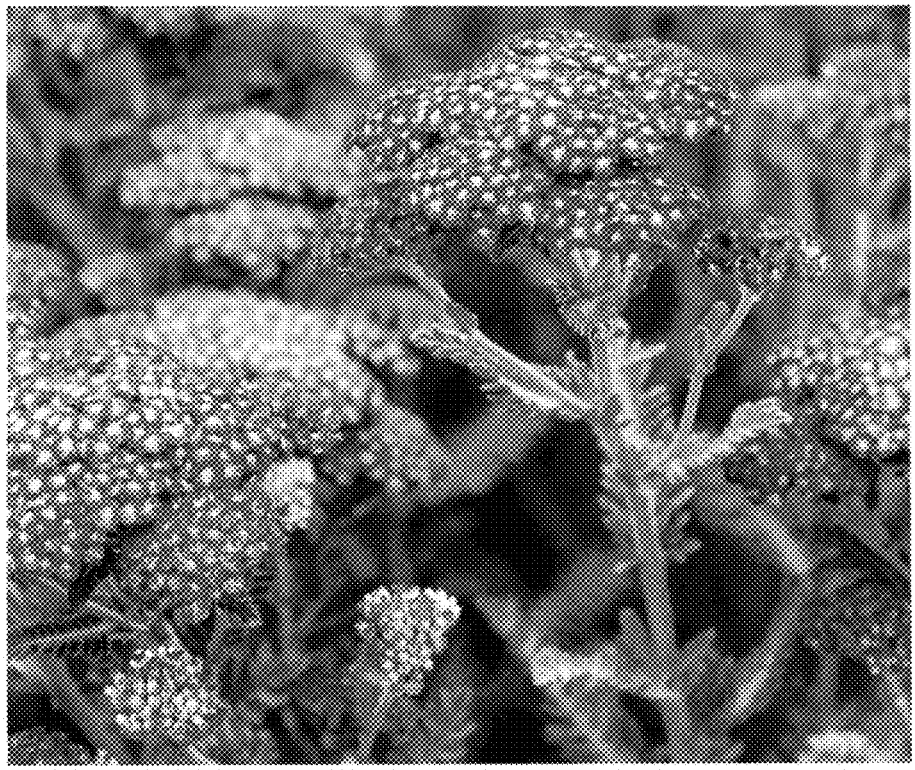
FIG. 2 shows a close-up of the inflorescences of the new plant.

The following description of the new plant is based on a three-year-old plant growing in a full-sun trial garden in Zeeland, MI, USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

*Parentage*.—parent 13-5-26.

*Asexual propagation*.—shoot tip cuttings, about 10 to 14 days to initiate roots; time to finish as #1 field grown size about 9 months.

*Plant habit*.—dense axillary branches; upright, heavily-branched, herbaceous, winter-hardy, perennial mound; up to 68 cm tall and 109 cm wide; average about 62 cm tall and about 100 cm across.

*Leaves*.—alternate; pinnatifid with lobules moderately incised; lanceolate; acute apex; base attenuate; lightly canescent adaxial and abaxial; sessile except proximal leaves.

*Leaf size*.—up to about 18 cm long and about 3.5 cm wide, average about 12.5 cm long and 2.8 cm wide; with individual lobes to about 12 mm wide and about 18 mm long.

*Leaf color*.—young expanding leaves adaxial nearest RHS N138A, abaxial between RHS 191A and RHS N138A; mature leaves adaxial lobes nearest RHS 137A, abaxial between RHS 138A and RHS 138B.

*Foliar fragrance*.—slightly herbal.

*Veins*.—pinnate; only adaxial and abaxial midrib obvious; abaxial midrib costate, adaxial midrib flat; adaxial sparsely lanulose, abaxial lanulose; midrib color adaxial nearest RHS 148D, abaxial midrib nearest RHS 146D.

*Petiole*.—when present—channeled; lanulose; to 2 cm long and 4 mm wide at base; color nearest RHS 146D.

*Stems*.—upright; cylindrical; lanulose to micro-pubescent; longitudinally ridged; color nearest RHS 137B proximally, distally striped RHS 191C and RHS 138B.

*Inflorescence*.—radiate; composite comprising of typically five or six ray florets and about 10 disk florets; on heavily branched terminal stems; individual inflorescence about 6 mm diameter, about 7 mm tall from bottom of involucral bracts to top of center disk tepals; attitude mostly upright; producing branched stems with about 300 inflorescences per stem forming flat-topped compound branched corymb; average branched corymb size about 12 cm across; flowering in upper 8 cm; branches to about 48 cm long and 3 mm diameter at base.

*Receptacle*.—about 2 mm diameter and 3 mm tall; color nearest RHS 148C.

*Inflorescence fragrance*.—not detected.

*Phyllaries*.—about 20 in two whorls; lanceolate; acute apex; truncate base; margin entire and ciliate; outer or lower set about 1.5 mm long and 1 mm across, inner set about 2.5 mm long and 1.5 mm across; glabrous adaxial, pubescent abaxial; tightly adpressed against ray petals.

*Phyllary color*.—adaxial and abaxial nearest RHS 137B with midrib and margin nearest RHS 155C.

*Flowering period*.—late June, for about seven weeks and repeating if deadheaded.

*Inflorescence longevity*.—4 to 6 days; about one week as a cut flower.

*Inflorescence buds*.—with ray florets still erect 7 mm tall and 3 mm across; ovoid.

*Inflorescence bud color*.—ray florets while still upright exposed abaxial ray floret ligule color nearest RHS 44B; phyllaries color nearest RHS 137B with midrib and margin nearest RHS 155C.

*Pedicel*.—cylindrical; micro-puberulent; strong; upright attitude; to about 6 mm long and 1 mm diameter; average about 4 mm long and 0.8 mm diameter.

*Pedicel color*.—color nearest RHS 147C.

*Ray florets*.—imperfect; sterile; typically about five per inflorescence, rarely six; ligule with limb and claw.

*Ray floret ligule*.—rounded with basal claw; apex rounded, emarginate with two notches about 0.2 mm deep, margin entire; base claw, attenuate; opening to a 90 ° angle to form flat face; glabrous adaxial and adaxial; about 5 mm long and about 4 mm wide; basal claw about 2 mm long and about 0.5 mm across; Young ray floret ligule color when first flat: adaxial nearest RHS 44B, abaxial nearest RHS 47C, and base nearest RHS 147C; Mature ray floret ligule color: adaxial between RHS 47B and RHS 53D; abaxial between RHS 50C and RHS 47D.

*Disk Florets*.—about 12 per capitulum; tubular; glabrous; consisting of five tepals, staminal tube, and pistil; size about 5 mm long by 1.5 mm wide at apex; Tepals: five; linear; fused in basal 4 mm; apex acute; margin entire; 3 mm long and 1 mm wide at fusion; Tepal color: distally between 162B and RHS 163B adaxial and abaxial, proximally nearest RHS 147D; Staminal tube: made up of five adnate stamens; about 3.5 mm long; Filaments: cylindrical; about 0.5 mm long and 0.1 mm diameter; color nearest RHS NN155A; Anther: about 1 mm long; color nearest RHS 17B; Pollen: fine, round, closest to RHS 17A; Style: bifid; cylindrical; exserted; about 4 mm long and 0.2 mm diameter; color proximally nearest RHS 157B and distally nearest RHS N186A; Stigma: bifid; reflexing as it matures; about 1.5 mm long; color nearest RHS N186A.

*Seed*.—flattened deltoid; acute apex and truncate base; surface glabrous; about 2.0 mm long and 0.7 mm across the base.

*Seed color*.—between RHS 165A and RHS 165B in the center and RHS 161D around the edges. *Achillea* 'Firefly Red Pop' is tolerant of winter temperatures as low as −35° C. and summer temperatures as high as 38° C. It is not known to be tolerant or susceptible to diseases and pests that are common to other *Achillea* cultivars.

I claim:

1. A new and distinct cultivar of *Achillea* plant named 'Firefly Red Pop' as described and illustrated.

* * * * *